United States Patent
Mitchell et al.

(10) Patent No.: US 7,913,261 B2
(45) Date of Patent: Mar. 22, 2011

(54) APPLICATION-SPECIFIC INFORMATION-PROCESSING METHOD, SYSTEM, AND APPARATUS

(75) Inventors: Oscar R. Mitchell, Pflugerville, TX (US); Robert Bradford Cohen, Austin, TX (US); Eleanor Coy, Austin, TX (US); Rajat Datta, Round Rock, TX (US); Randall Findley, Austin, TX (US); James Garrett, Austin, TX (US); Richard Goble, Cedar Creek, TX (US); Greg North, Austin, TX (US); Daniel Reents, Dripping Springs, TX (US); Leslie Zsohar, Round Rock, TX (US)

(73) Assignee: nCipher Corporation, Ltd., Stoneham, MA (US)

( * ) Notice: Subject to any disclaimer, the term of this patent is extended or adjusted under 35 U.S.C. 154(b) by 818 days.

(21) Appl. No.: 10/068,295

(22) Filed: Feb. 5, 2002

(65) Prior Publication Data
US 2002/0191604 A1    Dec. 19, 2002

Related U.S. Application Data (60) Provisional application No. 60/288,015, filed on May 2, 2001, provisional application No. 60/300,957, filed on Jun. 26, 2001, provisional application No. 60/300,955, filed on Jun. 26, 2001, provisional application No. 60/326,266, filed on Oct. 1, 2001, provisional application No. 60/326,252, filed on Oct. 1, 2001, provisional application No. 60/326,251, filed on Oct. 1, 2001, provisional application No. 60/326,250, filed on Oct. 1, 2001.

(51) Int. Cl.
*G06F 3/00* (2006.01)
*G06F 11/30* (2006.01)
*G06F 11/00* (2006.01)

(52) U.S. Cl. .............. 719/310; 713/189; 726/22
(58) Field of Classification Search .......... 719/310; 713/200, 189; 455/40; 718/105; 709/213; 726/22
See application file for complete search history.

(56) References Cited

U.S. PATENT DOCUMENTS

| | | | |
|---|---|---|---|
| 4,799,149 A | | 1/1989 | Wolf |
| 5,386,471 A | * | 1/1995 | Bianco .................. 713/162 |
| 5,542,061 A | | 7/1996 | Omata |
| 5,699,537 A | | 12/1997 | Sharangpani et al. |
| 5,724,279 A | | 3/1998 | Benaloh et al. |
| 5,764,554 A | | 6/1998 | Monier |
| 5,764,912 A | * | 6/1998 | Rosborough .............. 709/224 |
| 5,983,299 A | | 11/1999 | Qureshi |
| 5,987,574 A | | 11/1999 | Paluch |
| 6,061,796 A | * | 5/2000 | Chen et al. ................ 726/15 |
| 6,088,453 A | | 7/2000 | Shimbo |
| 6,097,955 A | * | 8/2000 | Bhat ..................... 455/445 |
| 6,134,244 A | | 10/2000 | Van Renesse et al. |

(Continued)

OTHER PUBLICATIONS

C2Net International, Troubleshooting, 1998.*

(Continued)

*Primary Examiner* — Lechi Truong
(74) *Attorney, Agent, or Firm* — John A. Fortkort; Fortkort & Houston P.C.

(57) ABSTRACT

An information-processing method for application-specific processing of messages. A message is received. Whether the message is in a selected application format is ascertained. If not, the message is routed to a next location. If so, the message is routed to a selected application processor, processed by the processor, and routed to the next location.

10 Claims, 7 Drawing Sheets

U.S. PATENT DOCUMENTS

| | | | |
|---|---|---|---|
| 6,141,705 A | 10/2000 | Anand et al. | |
| 6,151,393 A | 11/2000 | Jeong | |
| 6,157,955 A | 12/2000 | Narad et al. | |
| 6,167,450 A * | 12/2000 | Angwin et al. | 709/227 |
| 6,341,299 B1 | 1/2002 | Romain | |
| 6,560,450 B1 * | 5/2003 | Rosenberg et al. | 455/316 |
| 6,578,147 B1 * | 6/2003 | Shanklin et al. | 713/200 |
| 6,687,732 B1 * | 2/2004 | Bector et al. | 709/200 |
| 6,889,249 B2 * | 5/2005 | Miloushev et al. | 709/213 |
| 7,694,152 B2 * | 4/2010 | Carr | 713/189 |

OTHER PUBLICATIONS

Menezes, A.J., et al "Efficient Implementation" from theHandbook of Applied Cryptography, (Boca Raton, CRS Press, 1997), pp. 591-607.

Dimitrov, V. and Cooklev, T., "Two Algorithms for Modular Exponentiation Using Nonstandard Arithmetics" IEICE Trans. Fundamentals, vol. E78-A, No. 1, Jan. 1995.

Koc, C.K. and Hung, C.Y., "Carry-Save Adders for Computing the Product AB Modulo N" Electronics Letters, vol. 26, No. 13, (Jun. 21, 1990), pp. 899-900.

Freking, W. L. and Parhi, K.K., "Montgomery Modular Multiplication and Exponentiation in the Residue Number System" Proc. 33rd Asilomar Conf. Signals Systems and Computer, Oct. 1999, pp. 1312-1316.

Tenca, A.F. and Koc, C.K., "A Scalable Architecture for Montgomery Multiplication" in: Koc, C.K and Paar, C., Cryptographic Hardware and Embedded Systems, CHES 99, Lecture Notes in Computer Science, No. 1717. 1998, New York, NY: Springer-Verlog, 1999.

Koc, C.K. and Acar, T., "Montgomery Multiplication in GF (2k)" 3rd Annual Workshop on Selected Areas in Cryptography, (Aug. 15-16, 1996), pp. 95-106.

Bajard, J.C., et al "An RNS Montgomery Modular Multiplication Algorithm" IEEE Transactions on Computer, vol. 47, No. 7, (Jul. 1998), pp. 766-776.

Eldridge, S.E., "A Faster Modular Multiplication Algorithm" International Journal of Computer Math, vol. 40, (1991), pp. 63-68.

Bossalaers, A.., et al "Comparison of Three Modular Reduction Functions" in Douglas R. Stinson, editor, Advances in Cryptology—CRYPTO '93. vol. 773 of Lecture Notes in Computer Science, (Aug. 22-26, 1993), pp. 168-174.

Montgomery, P.L., "Modular Multiplication Without Trial Division" Mathematics of Computation, vol. 44, No. 170 (Apr. 1985), pp. 519-521.

Koc, C.K., et al "Analyzing and Comparing Montgomery Multiplication Algorithms" IEEE Micro, vol. 16, Issue 3, (Jun. 1996), pp. 26-33.

Kornerup, P., "High-Radix Modular Multiplication for Cryptosystems" Department of Mathematics and Computer Science, (1993), pp. 277-283.

Sunar, B. and Koc, C.K., "An Efficient Optimal Normal Basis Type II Multiplier" Brief Contributions, IEEE Transactions on Computers, vol. 50, No. 1, (Jan. 2001), pp. 83-87.

Koc, C.K., "Comments on 'Residue Arithmetic VLSI Array Architecture for Manipulator Pseudo-Inverse Jacobian Computation'" Communications, IEEE Transactions on Robotics and Automation. vol. 7, No. 5, (Oct. 1991), pp. 715-716.

Savas, E. and Koc, C.K., "The Montgomery Modular Inverse-Revisited" IEEE Transactions on Computers, vol. 49, No. 7, (Jul. 2000), pp. 763-766.

Walter, C.D., "Montgomery's Multiplication Technique: How to Make it Smaller and Faster" in Cryptographic Hardware and Embedded Systems—CHAS 1999, C. Paar (Eds.). K. Ko, Ed. 1999, Springer, Berlin Germany, pp. 61-72.

Oh, H. and Moon, J., "Modular Multiplication Method" IEE Proc.-Comput. Digit.Tech., vol. 145, No. 4, (Jul. 1998), pp. 317-318.

Blum, T., "Modular Exponentiation on Reconfigurable Hardware" Master's thesis, ECE Department, Worcester Polytechnic Institute, Submitted to Faculty Apr. 8, 1999, Published May 1999. Retrieved from the Internet <URL: http://www.wpi.edu/pubs/ETD/Available/etd-090399-090413/unrestricted/blum.pdf>.

Marwedel, P., et al. "Built in Chaining: Introducing Complex Components into Architectural Synthesis." Apr. 1996. Proceedings of the ASP-DAC, 1997. (online). Retrieved from the Internet <URL: http://eldorado.uni-dortmund.de:8080/FB4/ls12/forshung/1997/aspdac/aspacPDF>.

Tiountchik, A., and Trichina, E., "RSA Acceleration with Field Programmable Gate Arrays" Lecture Notes in Computer Science, vol. 1587, pp. 164-176. Retrieved from the Internet: <URL:http://citeseer.nj.nec.com/274658.html>.

Menezes, A.J., et al "Handbook of Applied Cryptography" Boca Raton, CRC Press, 1997.

\* cited by examiner

APPLICATION-SPECIFIC INFORMATION-PROCESSING METHOD, SYSTEM, AND APPARATUS

CROSS-REFERENCE TO RELATED APPLICATIONS

This application claims the benefit of the following U.S. Provisional Applications, all of which are hereby incorporated by reference, and the content of which are not necessarily identical to the content of this application:

| Atty. Dkt. # | Ser. No. | Title | Filing Date |
|---|---|---|---|
| COMMONLY OWNED AND PREVIOUSLY FILED U.S. PROVISIONAL PATENT APPLICATIONS | | | |
| 501143.000005 | 60/288,015 | Method and Apparatus for Shotgun Multiplication and Exponentiation | May 2, 2001 |
| 501143.000010 | 60/300,957 | Method and Residue Calculation Using Casting Out | June 26, 2001 |
| 501143.000011 | 60/300,955 | Add-Drop Layer 3 Ethernet Ring Switch | June 26, 2001 |
| 501431.000014 | 60/326,266 | Application Specific Information Processing System | Oct. 1, 2001 |
| 501143.000015 | 60/326,252 | Efficient Use of DRAM-Based Devices For Small Discontiguous Memory Accesses | Oct. 1, 2001 |
| 501143.000016 | 60/326,251 | Exponentiation Engine | Oct. 1, 2001 |
| 501143.000017 | 60/326,250 | Method for Squaring | Oct. 1, 2001 |

The current application shares some specification and figures with the following commonly owned and concurrently filed applications, all of which are hereby incorporated by reference:

| Atty. Dkt. # | Ser. No. | Title | Filing Date | Status |
|---|---|---|---|---|
| COMMONLY OWNED AND CONCURRENTLY FILED U.S. NONPROVISIONAL PATENT APPLICATIONS | | | | |
| LYNR002US0 | 10/068,294 | Ring Arithmetic Method, System, and Apparatus | Feb. 5, 2002 | Issued May 15, 2007 U.S. Pat. No. 7,218,734 |

The benefit of 35 U.S.C. §120 is claimed for all of the above referenced commonly owned applications. The contents of the applications referenced in the tables above are not necessarily identical to the contents of this application.

All references cited hereafter are incorporated by reference to the maximum extent allowable by law. To the extent a reference may not be fully incorporated herein, it is incorporated by reference for background purposes and indicative of the knowledge of one of ordinary skill in the art.

BACKGROUND OF THE INVENTION

1. Field of the Invention

The present invention relates generally to an information-processing system and in particular to an information-processing system for use in a network which processes information for use by one or more specific applications.

2. Description of Related Art

Advances in the field of application-specific information-processing systems have solved many issues. But problems remain. The present invention solves some of the remaining problems.

An example of a traditional implementation of a network protocol stack includes a hardware-link layer—also called a transport layer—that verifies and delivers packets to a software protocol stack. Each packet is selected based on its frame format and stripped of any frame header that may be present. Each packet is then sent to the appropriate protocol stack and subsequently to the appropriate application.

If the implementation is a single processor implementation, the processor shepherds each packet through each software stack, processing one packet at a time, and queuing other packets for later processing. In a multiple processor implementation, each processor also acts on one packet at a time. Access to shared data structures is carefully serialized, so the total number of packets being processed is limited to the number of processors available.

One example is a TCP packet's handling on a TCP/IP Ethernet network. A hardware network interface card checks and delivers the incoming TCP packet to a software stack. The TCP packet's Ethernet frame header is removed, and the packet is sent to an IP stack. Then its IP header is verified and removed, and the packet is sent to a TCP stack. The packet's TCP header is verified and removed, and the packet's data is sent to an application. This process is used in many embedded devices.

BRIEF SUMMARY OF THE INVENTION

A preferred embodiment is an information-processing method for application-specific processing of messages. A message is received. Whether the message is in a selected application format is ascertained. If not, the message is routed to a next location. If so, the message is routed to a selected application processor, processed by the processor, and routed to the next location.

BRIEF DESCRIPTION OF THE DRAWINGS

The following drawings form part of the present specification and are included to further demonstrate certain aspects of the present invention. The figures are not necessarily drawn to scale. The invention may be better understood by reference to one or more of these drawings in combination with the detailed description of specific embodiments presented herein.

DETAILED DESCRIPTION OF PREFERRED EMBODIMENTS

In a preferred embodiment, an information-processing system encodes and decodes data to and from a network protocol. Processing steps select and prepare the data for use by one or more specific applications.

In a preferred embodiment, an information-processing system encodes and decodes multiple network protocols. The information-processing system uses data being carried over the network for an application. The information-processing system includes hardware state machines or simple programmable processors as modules. Each such module specializes in a specific task. The modules are interconnected to process data in a generally pipelined fashion. Thereby, module specialization contributes to the information-processing system's capability of processing networking traffic at very high speeds.

Modules are described as physically distinct entities for convenience, but they are computational units. As such, they may have any physically adequate embodiment. Some examples include being embodied in software running on a general processing device, in hardwired circuits, in a combination of software and hardware, etc. Therefore, any number of modules may be encapsulated in a single IC. Similarly, the functionality of a single module may be enabled using several physical devices. Modules are described by the computations they perform and not by the techniques, mechanisms, and combinations and subcombinations thereof that achieve the specified computations. In a preferred embodiment, the modules are hardware state machines or simple programmable processors.

Figure 1:
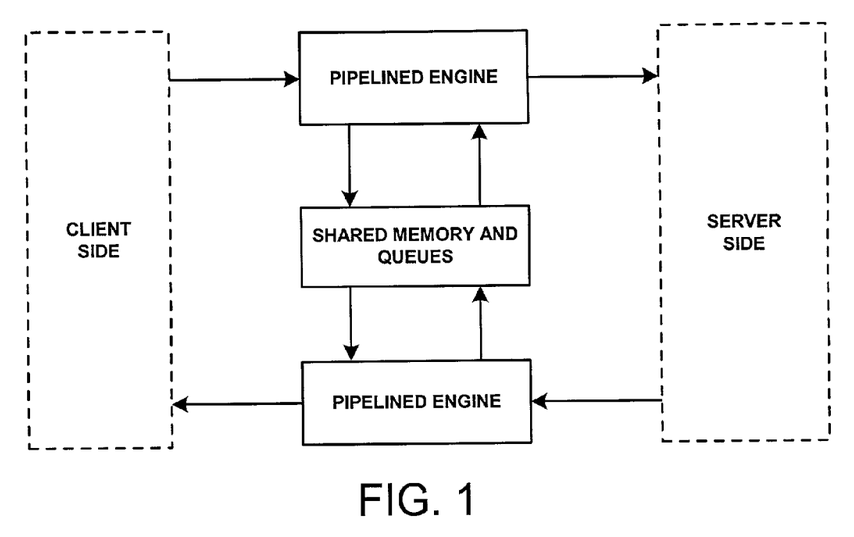
FIG. 1 shows a high-level diagram of an information-processing system, in accordance with an embodiment of the present invention.

FIG. 1 shows a high-level diagram of an information-processing system, according to a preferred embodiment. In this embodiment, network data in the form of packets pass from the client side through a physical-link-level layer to the information-processing system—also called a pipelined engine— where the packets are processed using shared resources, such as shared memory and queues, and then passed to the server side.

In a preferred embodiment, multiple networking modules work in conjunction. A packet is received at an information-processing system from a physical-link-level layer and then passes through the modules, typically in sequential fashion. The networking modules decode various network protocol frame headers. The application modules process the data contained in the packets.

Some examples of network protocols are described in Appendix A of this description. It is contemplated that for any message-based network protocol, an embodiment could be implemented to process messages of that protocol without departing from the spirit of the invention.

Application streams can have state information that is collected and processed over the lifetime of the application stream. In some preferred embodiments, an application service device (ASD) performs a function on one or more application streams. Examples of ASDs include SSL/TLS processors, IPSEC processors, TCP offload engines, content accelerators, firewalls, load balancers, IP-based storage devices, etc.

Figure 6:
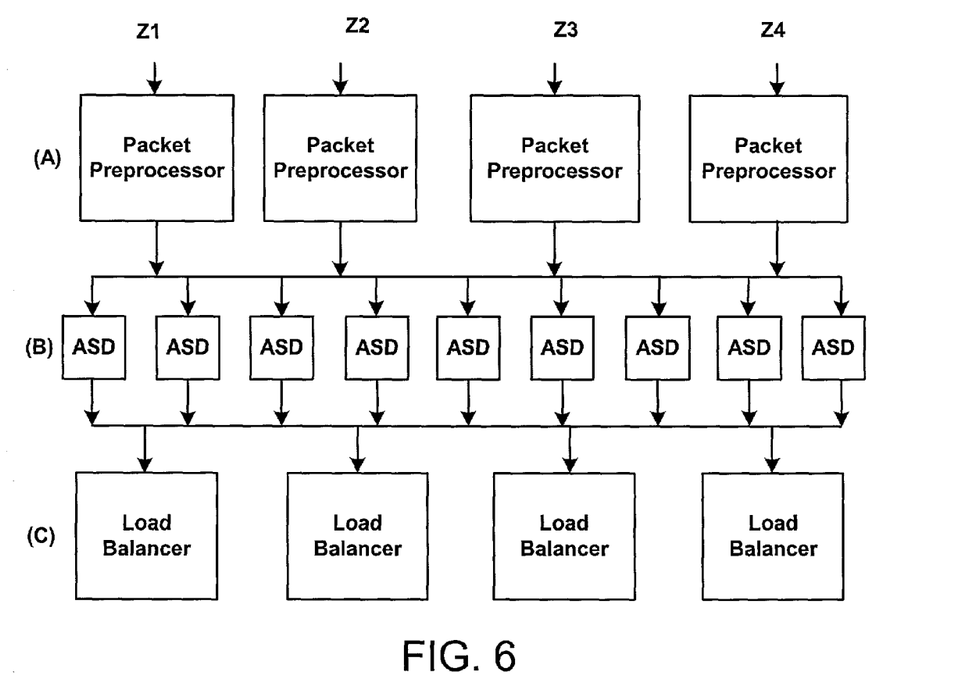
FIG. 6 shows a high-level diagram of a fabric and application service devices, in accordance with an embodiment of the present invention.

State information is collected from each packet to encrypt or decrypt subsequent packets. Typically, increasing bandwidth is difficult, further increasing the importance of achieving higher speeds via other solutions. As illustrated in FIG. 6, Group B, an ASD may perform a service via a number of connected devices. For example, a service that requires multiple tasks could be implemented using a different device to perform each service. In a preferred embodiment, an SSL/TLS device handles SSL/TLS handshakes and encryptions over a TCP/IP network. The SSL/TLS device includes a handshake unit and a data encryption unit. The handshake unit performs the handshake, while the data encryption unit performs encryption.

In a preferred embodiment, a collection of fabric elements is included in a fabric. The fabric switches each application stream to an appropriate application service device. An application stream is a stream of application data between a set of end points. Examples of application streams include an SSL/TLS connection between a web browser and a web server, e-mail transfers, etc. In this preferred embodiment, the data from each application stream is kept separate from the data of other application streams. Application data can originate at any of the end points and flow to any other end point. Typically, an application stream can be processed by a subset of the ASDs. An example of this is a session in which all data packets of an SSL/TLS session require handling by the particular ASD that handled that session's SSL/TLS handshake.

FIG. 6 illustrates an embodiment system where packets are gathered from one or more different networks, processed by ASDs and passed out to one or more networks for further processing. Related packets may arrive over different networks. The fabric elements in Group A are responsible for gathering information from related packets and routing them to the appropriate ASDs in Group B. The elements in Group C are responsible for taking the processed output from the ASDs and passing them on to one or more networks.

Group A preprocessing elements are each responsible for receiving packets from a network. There may be one or more Group A elements. For example, there will typically be more than one Group A element in a large installation where multiple network connections are used to avoid a single point of failure. The Group A preprocessing elements are responsible for routing different type of packets to different ASDs in Group B.

Group B ASDs are each specialized protocol processors. One or more may be SSL/TLS processors, and one or more may be VPN processors. Group C elements are responsible for load balancing streams of packets from the ASDs to back-end servers. There may be one or more Group C elements.

So Group A and Group C represent a fabric that includes fabric elements. As stated above, Group B represents ASDs. Referring now to a preferred embodiment represented by Group A, Group B, and Group C, each module processes a single packet or data block at a time. The result of the processing is then output from the module and can then be passed to another module for further processing. The modules have access to a shared memory area, which need not be the case in every preferred embodiment. The modules also notify each other with messages about global state change conditions, which need not be the case in every preferred embodiment.

Referring now to a preferred embodiment depicted in FIG. 1, an information-processing system may be implemented as a pipeline. In the pipeline, modules are related sequentially such that the output of each module—except the last module—is typically the input of its succeeding module. However, the modules are adapted to make decisions and accordingly the pipeline analogy does not apply absolutely. While the general flow of information will typically be from one module to the next in a linear sequence, the relatedness of the modules creates a more complex connectivity design than a simple pipeline.

In a preferred embodiment, each module processes a single packet at a time, and each packet is processed by a single module at a time. Each module is assigned a time budget, so that the process(es) performed by the module are completed in a known number of clock cycles. The pipeline gates the flow of packets through the modules so that as each module outputs a packet, the module receives a new packet for processing. Each module's time budget is set relatively small in the design stage so that module operations are rendered relatively simple. Therefore, design of each module is driven by its time budget, network speed requirement, packet size, and task complexity.

Figure 2:
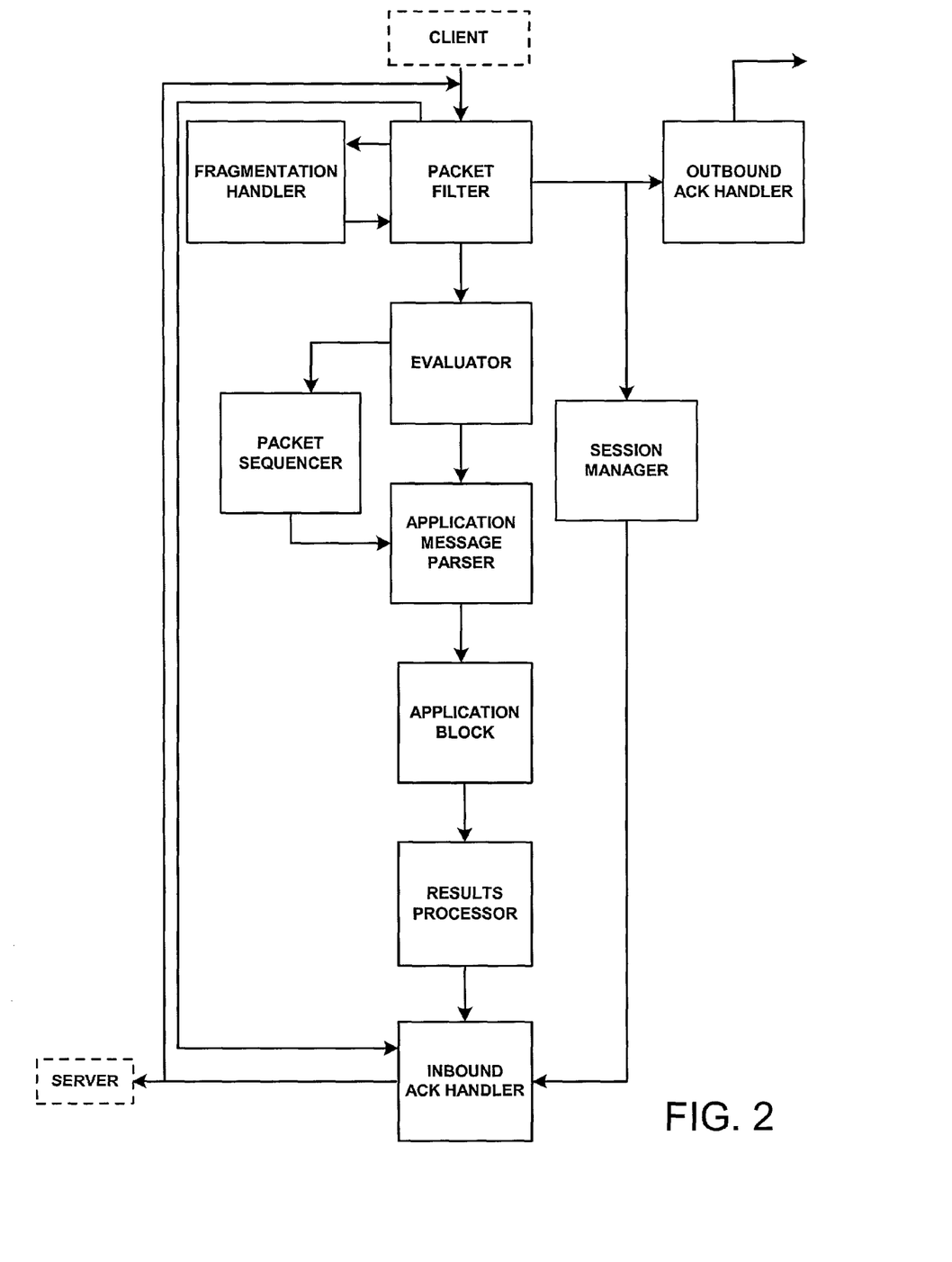
FIG. 2 shows a high-level diagram of a client to server proxy, in accordance with an embodiment of the present invention.

For example, in FIG. 2, the Session Manager module establishes a new connection in processing a SYN packet. SYN packets are exchanged in establishing a TCP connection. Simultaneously, the Evaluator module checks a TCP packet to determine if it is in-sequence or out-of-sequence and the Packet Filter module checks the header of a packet to determine to which of the other modules the packet should be forwarded.

There are many advantages to this design approach, some of which are described. The modules are simpler and relatively independent which makes them easier to specify, design, and test. Also, the information-processing system may be tailored to a specific application or set of applications so that network packets that are part of different application streams can be quickly passed-thru or dropped without affecting the performance of the rest of the device.

For example, in a preferred embodiment, SSL/TLS information is processed. UDP packets and packets for non-managed ports are filtered out by the packet filter module, so they are not processed by any other modules. This design characteristic makes it easier to quantify the performance characteristic of each module and the entire information-processing system.

In a preferred embodiment of the invention, represented by FIG. 2, an information-processing system has been designed to process SSL/TLS connections. In this SSL/TLS information-processing system, a certificate table is defined accordingly. Each entry in the certificate table can contain an external IP address, a port number, certificate information, a server IP address, and a server port number. The external IP address and port number constitute a managed port that is used by each client attempting to establish an SSL/TLS connection. The certificate information contains a public certificate and associated private keys necessary for the SSL/TLS handshake. When a connection is made with a client over the managed port for an entry, a matching connection is made to the server port that is given by the server IP address and port number. Any data that arrives from the client over the SSL/TLS connection is decrypted and then forwarded to the server over the matching connection.

In the context of this description, two tasks are said to be processed concurrently if both tasks are processed at generally the same time, preferably in the same clock cycle. For example, in FIG. 2, a Packet Filter module can be determining whether a packet is for a managed port concurrently with an Evaluator module determining whether another packet is in-sequence or out-of-sequence.

In a preferred embodiment, an Evaluator module determines whether a packet is in-sequence or out-of-sequence. A sequential stream of packet-based data includes packets, each having an explicit or implicit sequence number specifying its place in the sequential stream. This characteristic allows the packets to be delivered in any order and requires the receiver to place the packets in order. For example, each TCP packet contains an explicit sequence number in its TCP frame header. Out-of-sequence packets can occur in many ways. For example, if a packet is dropped due to congestion, hardware failure, or other cause, the transmitter will not receive an acknowledgement of receipt of the dropped packet. After a period of time without receipt of an acknowledgement, the transmitter will resend the packet.

In a preferred embodiment, an information-processing system SSL/TLS proxy has two elements: a client to server (CS) proxy and a server to client (SC) proxy. Modules for the CS proxy, represented by FIG. 2, may be implemented as follows.

A CS Packet Filter module filters IP packets arriving from the client. If an arriving packet is not intended for a managed port, it is routed immediately to the server. SYN, FIN and RST packets are sent to a CS Session Manager module for establishing or breaking a connection, as appropriate. Arriving Ack packets are directly forwarded to the CS Inbound Ack Handler.

The CS Session Manager module is responsible for accepting the client's TCP connections from the CS Packet Filter and will establish a matching connection with the server in accordance with the Certificate table. The CS Session Manager will terminate a connection upon receipt of a FIN or RST packet or upon time-out.

The CS Packet Filter module sends each IP packet fragment to a CS Fragmentation Handler module. Once all the fragments of a fragmented packet are received, the fragmented packet is reassembled and sent back to the CS Packet Filter module for processing.

SSL/TLS handshake messages are created in response to handshake messages from the client. They are sent in reply to the client via the CS Outbound Ack Handler module.

TCP packets are sent to a CS Evaluator module for determination of whether they are in-sequence or out-of-sequence. In-sequence packets are sent to an CS Application Message Parser module. Out-of-sequence packets are sent to a CS Packet Sequencer module. The CS Packet Sequencer module re-sequences packets and then passes them on in proper sequence to the CS Application Message Parser module for further processing.

Figure 4:
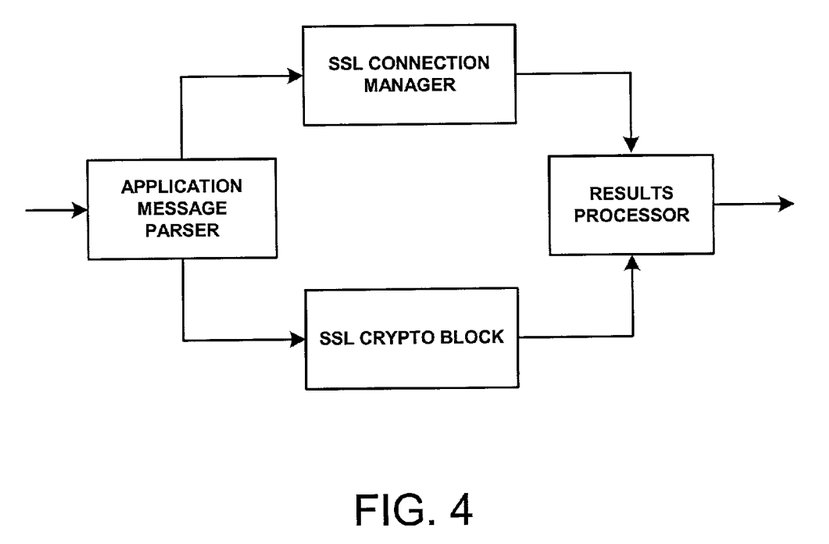
FIG. 4 shows a lower-level diagram of a section of FIG. 2, in accordance with an embodiment of the present invention.
Figure 5:
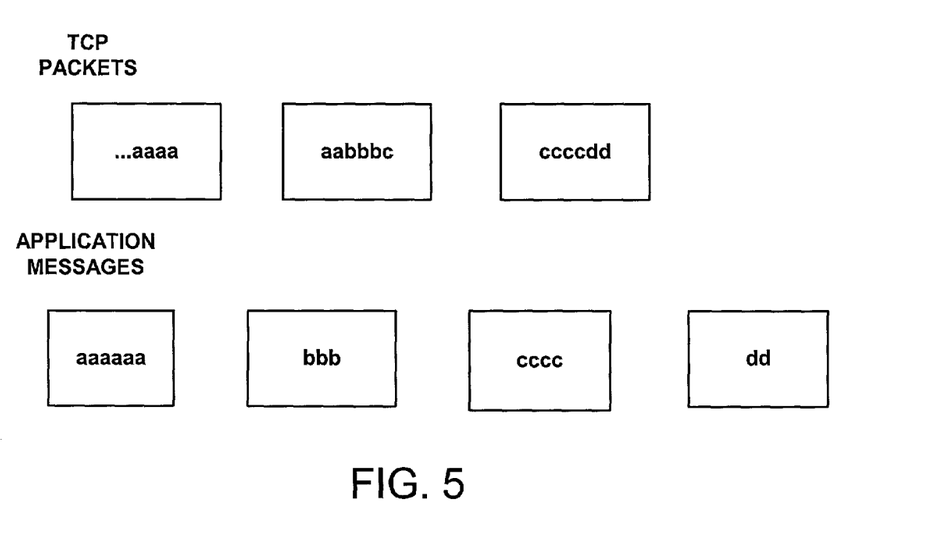
FIG. 5 illustrates how application messages are parsed across TCP packets, in accordance with an embodiment of the present invention.

TCP packets can form a stream of data that can contain SSL/TLS messages. As shown in FIG. 5, the boundaries of a TCP packet do not necessarily align with the boundaries of an SSL/TLS message. The CS Application Message Parser module is responsible for combining and splitting TCP packets to form SSL/TLS messages. In FIG. 2, the CS Application Message Parser module sends packets to the CS Application Block module, and the CS Application Block module sends packets to the Results Processor. The communication relationships of these three modules are represented at a lower level in FIG. 4. The CS Application Message Parser module sends SSL/TLS handshake packets to a CS SSL/TLS Connection Manager module, and SSL/TLS data packets to a CS SSL/TLS Crypto Block module.

The CS SSL/TLS Connection Manager module performs an SSL/TLS handshake using Certificate Information for this managed port from a Certificate Table. The CS SSL/TLS Connection Manager module receives all the handshake messages from the client and creates handshake messages in response. The output from the CS SSL/TLS Connection Manager module will be to establish an SSL/TLS connection or refuse it. This block contains the public key cryptographic elements necessary for SSL/TLS.

The CS SSL/TLS Crypto Block module first receives SSL/TLS data messages from the client over an established SSL/TLS connection and then encryption processes the SSL/TLS data messages. The encryption processed SSL/TLS data messages are subsequently output to the CS Results Processor module.

The CS Results Processor module receives the output of the CS SSL/TLS Connection Manager module and SSL/TLS Crypto Block module. The CS Results Processor module sends decrypted SSL/TLS data to the server via the CS Inbound Ack Handler module.

The CS Inbound Ack Handler module and the CS Outbound Ack Handler module are responsible for tracking the Acks for packets sent out over the network to the server or client, respectively. Ack packets are sent over the network to the client via the CS Outbound Ack Handler module. If an Ack is not received within a set period of time, the packet is resent. If an Ack is not received after repeated attempts, the session is terminated and an error condition is raised.

In the same preferred embodiment, modules for the server to client (SC) proxy, represented by FIG. 3, may be implemented as follows.

An SC Packet Filter module receives packets from the server. For each packet, an SC Packet Filter determines whether the packet is a TCP packet and whether the packet is intended for the proxy server. If the packet is not a TCP packet that is intended for the proxy server, the packet is forwarded immediately out to the client. If the packet is an FIN packet or an RST packet, it is sent to an SC Session Manager module.

In this preferred embodiment, the server never connects to the proxy. Therefore, the SC Session Manager does not handle SYN packets: connection attempts are rejected immediately. Rather, the SC Session Manager module only manages FIN packets, RST packets, and time-out packets that terminate a session. The CS Session Manager is notified about these Session termination events.

Figure 3:
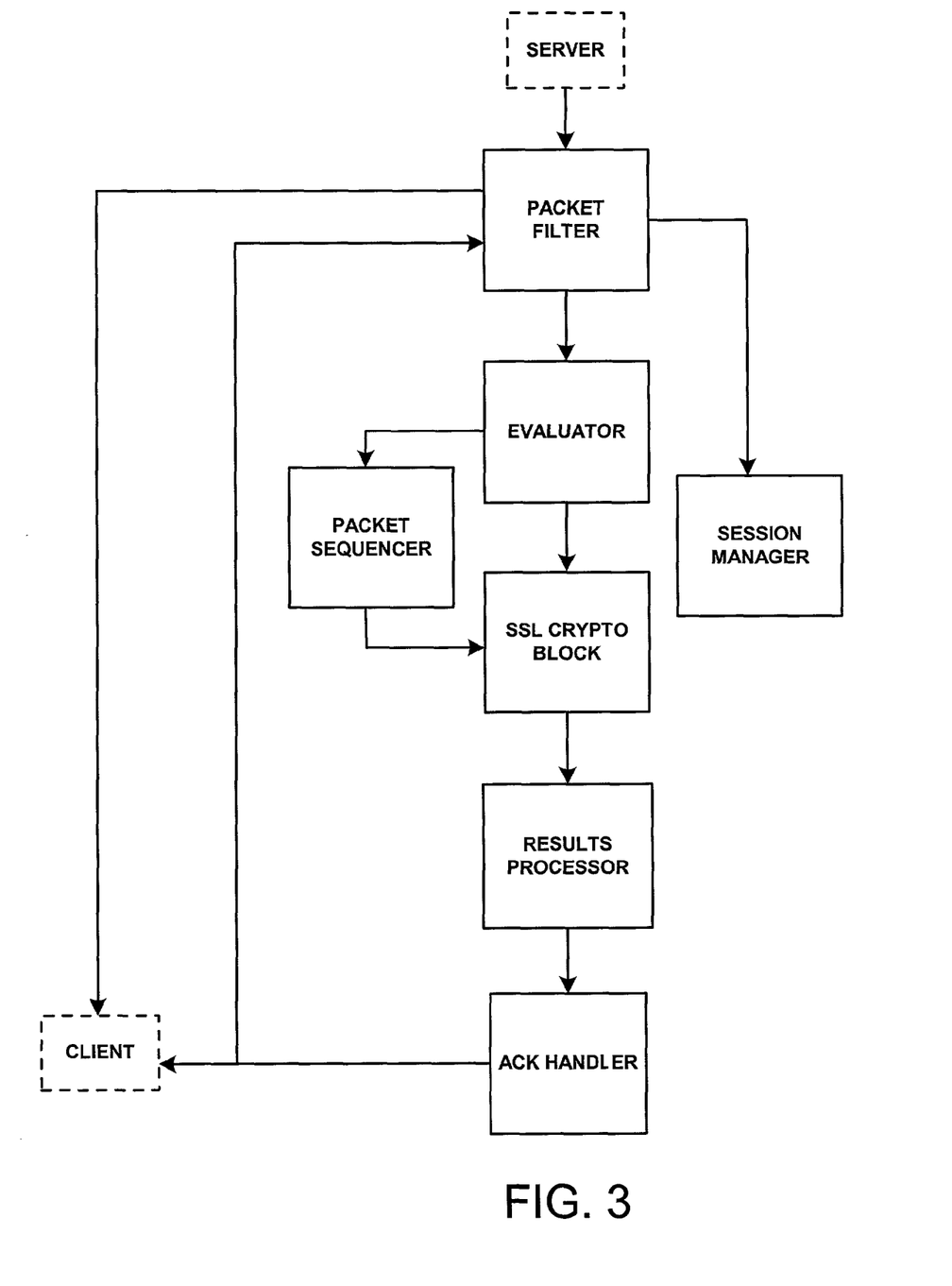
FIG. 3 shows a high-level diagram of a server to client proxy, in accordance with an embodiment of the present invention.

The SC Packet Filter module sends each IP packet fragment to an SC Fragmentation Handler module (not shown in FIG. 3). Once all the fragments of a fragmented packet are received, the fragmented packet is reassembled and sent back to the SC Packet Filter module for processing.

TCP packets are sent to an SC Evaluator module for determination of whether they are in-sequence or out-of-sequence. In-sequence packets are sent to an SC SSL/TLS Crypto Block module. Out-of-sequence packets are sent to an SC Packet Sequencer module. The SC Packet Sequencer module re-sequences packets and then passes them on in proper sequence to the SC SSL/TLS Crypto Block module for further processing.

The SC Crypto Block module encrypts the data from each incoming TCP packet and places the encrypted data in an SSL/TLS message. The SC Crypto Block module then forwards the SSL/TLS message to the SC Results Processor module.

The SC Results Processor module places the SSL/TLS message in a TCP packet frame and sends it to the SC Ack Handler module.

The SC Ack Handler module sends the TCP packet to the client over the link transport layer and awaits an Ack for a time period. If an Ack is not received within the time period, the packet is resent. Repeated failures causes the SC Ack Handler module to declare an error event and close the connection.

A preferred embodiment also provides for superior bandwidth scaling. The local service devices can operate at a lower bandwidth. A simpler design may be used to accomplish complex application processing, with a simpler implementation. ASDs may be connected in parallel as in FIG. 6, Group B to achieve superior aggregate bandwidth. And they may be connected serially to achieve superior aggregate capacity. Where each ASD is capable of a certain quantity of bandwidth (x), and several devices (n) are connected to the fabric as in FIG. 6, Group A the combined system achieves n times x bandwidth.

This preferred embodiment furthermore provides better path resiliency. An application stream can arrive over multiple networks and channels, where the fabric operationally combines them. Packets of a single application stream will be sent to the same ASD. Where different streams arrive at the fabric having different protocols, the data is converted to a single protocol. For example, where an ASD is only capable of processing IPV4 and that ASD interfaces with a network carrying IPV6 traffic, fabric elements are used to perform the conversion between IPV6 and IPV4.

Figure 7:
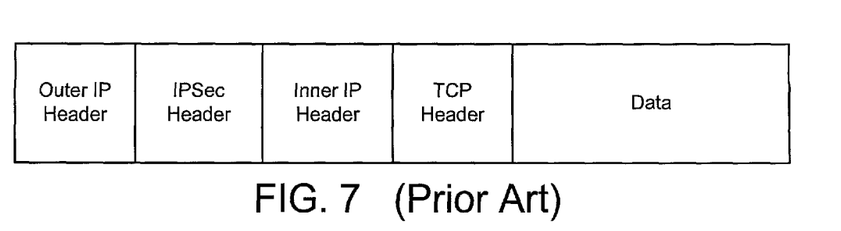
FIG. 7 shows the organization of a packet protected by IPSec in tunnel mode, in accordance with an embodiment of the PRIOR ART.

One embodiment is a tunnel-mode IPSec VPN. FIG. 7 shows an example of an IP packet protected by IPSec in tunnel mode. The outer IP header is used to actually transmit a packet over an unsecured network. One unsecured network is the Internet. The IPSec header contains the authentication information.

Security Associations (SA) are the contract between the two ends of an IPSec connection. SAs determine the specific IPSec protocols used to secure packets, keys, and the duration for which the keys are valid. Each connection has a pair of SAs, one for incoming packets and one for outgoing packets. An SA database (SADB) is used to hold the SA.

Figure 8:
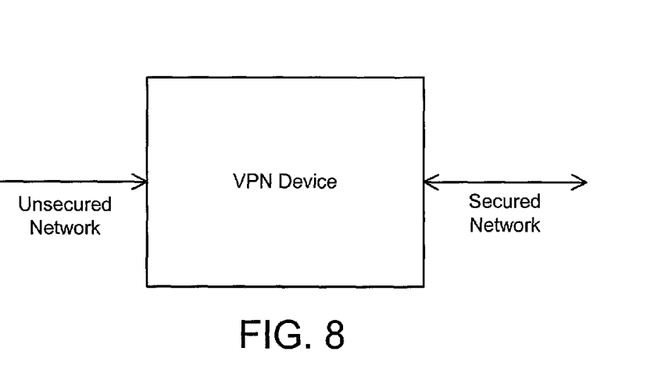
FIG. 8 shows a block diagram of a possible VPN device, in accordance with an embodiment of the present invention.

FIG. 8 is a block diagram of a possible VPN device. It connects a secured network (accessible only by trusted parties) to an unsecured network. The device (1) provides the protection necessary to authenticate clients and (2) protects the data on the unsecured network by encrypting packet contents.

The VPN device offers secure channels over the unsecured network. It is possible that unsecured channels are also allowed between clients on the unsecured network and clients on the secured networks. Those channels, if they travel through the VPN device, can be passed through without interference.

Figure 9:
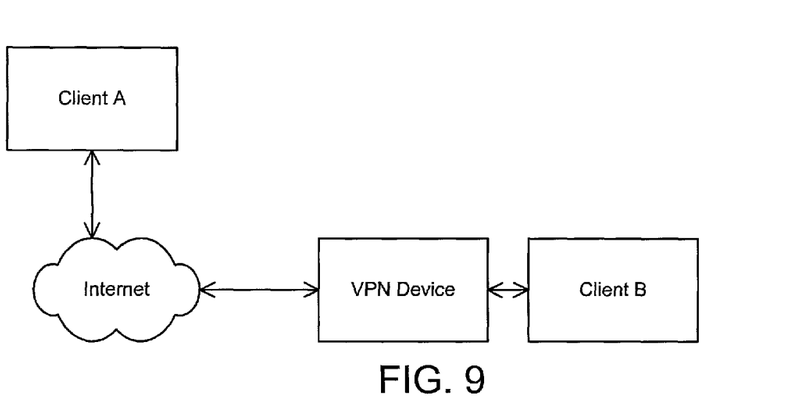
FIG. 9 shows a possible VPN scenario, in accordance with an embodiment of the present invention.

FIG. 9 shows an embodiment where a VPN device is used. Packets transmitted from Client A to Client B—and from Client B to Client A—over the Internet, an unsecured network, are protected by the IPSec authentication and encryption services offered by the VPN device on the Client B side and possibly by software on the Client A side.

When the VPN device receives a packet from Client A over the unsecured network, it authenticates the sender using the IPSec header, decrypts the packet contents, and passes the decrypted packet over the secured network to the receiving Client B using the inner IP header.

When the VPN device receives a packet from Client B over the secured network, it encapsulates the entire packet by encrypting it, adding an IPSec header, adding an outer IP header, and transmits it over the unsecured network.

Figure 10:
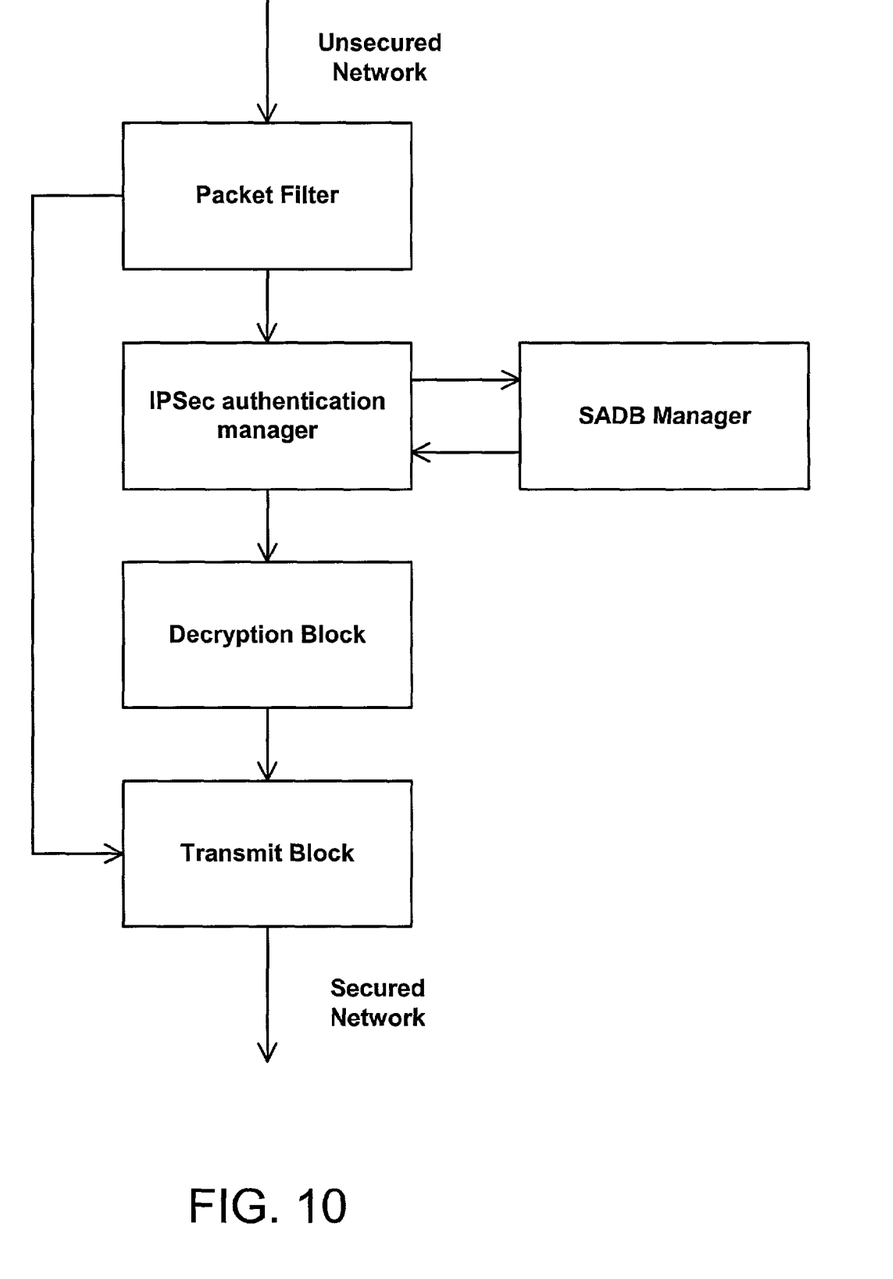
FIG. 10 shows a possible VPN device implementation, in accordance with an embodiment of the present invention.

FIG. 10 is a block diagram of a possible VPN device implementation for incoming packets. A packet filter is responsible for receiving IP packets, recognizing which ones are on secured channels, as well as which have been fragmented. Packets for unsecured channels are sent on a bypass path directly to the transmit block for transmission to the secured network. Fragmented IP packets are sent to a fragmentation handler that FIG. 10 does not show. Packets for secure channels are sent to the IPSec authentication manager. The IPSec authentication manager authenticates the client transmitting the packet, and passes the contents of the packet, including the inner IP header, TCP header, and data blocks, to the decryption block. The authentication manager also communicates with the SADB block to retrieve the incoming SA. The authentication manager may comprise multiple blocks each responsible for a specific task involved with managing SAs.

The decryption block decrypts the packet content using the decryption algorithm and other information, as specified by the authentication manager. The decrypted packet is then transmitted on the secured network by the transmit block.

Each block described must process a packet within a specific time period. If the processing within a block is too complicated to meet its time budget, it must be split and then component blocks should meet the time budget for individual packets. Since each block is capable of processing different packets at the same time, total system throughput in terms of packets per time period goals should be met.

Figure 11:
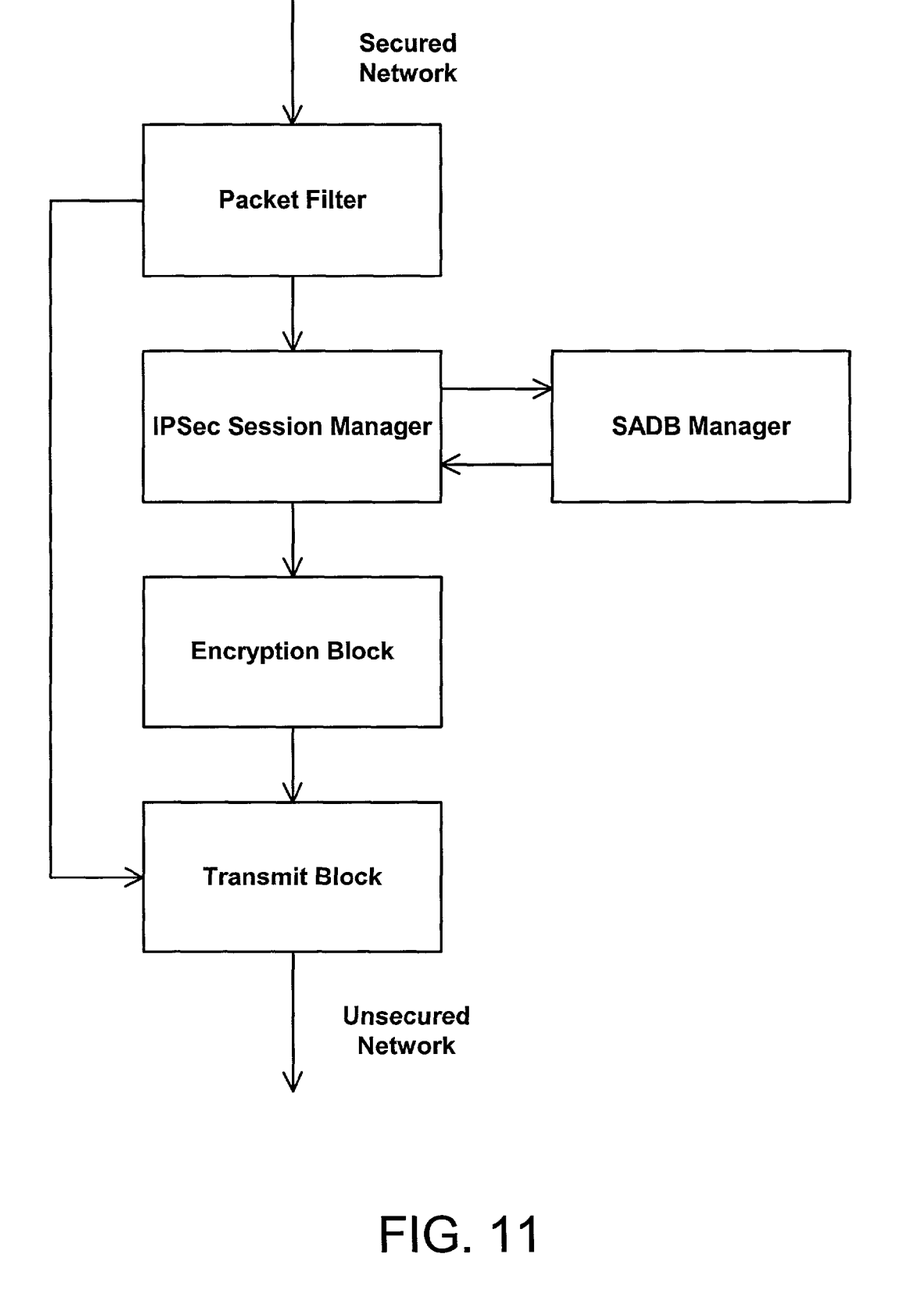
FIG. 11 shows an outgoing packet handler, in accordance with an embodiment of the present invention.

FIG. 11 describes an outgoing packet handler. The packet filter recognizes whether a packet is for a secured channel. If not, the packet is immediately routed to the transmit block. Otherwise, the IPSec session manager communicates with the SADB manager to fetch the necessary outgoing SA for the corresponding secure channel. The session manager gathers and builds the necessary information for authenticating this packet.

The Encryption block takes the authentication information, builds the outer IP header and IPSec header, and encapsulates the received packet to organize the IPSec packet as shown in FIG. 7. Under certain conditions, the outgoing packet could be big enough to be fragmented into two encapsulated packets. The transmit block then transmits the IPSec encapsulated packet onto the unsecured network.

As will be recognized by those skilled in the art, the innovative concepts described in the present application can be modified and varied over a tremendous range of applications, and accordingly the scope of patented subject matter is not limited by any of the specific examples given. For example, an ASD, with its described functions, could be physically incorporated into a firewall device, or could be incorporated into a network interface device that is physically located in a server system. Multiple ASDs can be implemented as one physical apparatus. ASDs could perform other data processing tasks instead of or in addition to decryption tasks.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provision of 35 U.S.C. §112, ¶6.

It should be apparent from the foregoing that an invention having significant advantages has been provided. While the invention is shown in only a few of its forms, it is not limited to those but is susceptible to various changes and modifications without departing from the spirit of the invention. Furthermore, while many contemplated modifications and variations have been explicitly referenced in this detailed description, they are not intended to be an exclusive listing of modifications and variations. It is contemplated that variations and modifications could be implemented to implement innumerable different preferred embodiments without departing from the spirit or scope of the claimed invention, and it is contemplated that such would be obvious to one of ordinary skill in the art.

APPENDIX A

Glossary

This Glossary defines words as they are used throughout this application. This Glossary lists base words rather than word variations. But the meanings of word variations—such as "connecting," "connect," and "connected" for the base word "connection"—are also given meaning according to their logical relationship to the base word.

"=" means equality or congruence, depending on the context. This is clear to typical practitioners of this technical area.

"~" means approximately.

"algorithm" means a process for completing a task. An encryption algorithm is the process, typically with mathematical characteristics, to encrypt and decrypt messages.

"ARP" means Address Resolution Protocol. To map an IP address into a hardware address, a computing device uses the ARP protocol which broadcasts a request message containing an IP address, to which a target computing device replies with both the original IP address and the hardware address.

"Asymmetric encryption" means encryption used in a public-private key cryptosystem.

"Asymmetric key cipher" means a public-private key cryptography system.

"Authentication" means the process of verifying that a file or message has not been altered in route from the distributor to the recipient(s).

"Cipher" means a cryptographic algorithm used to encrypt an decrypt files and messages.

"Ciphertext" means the disguised (or encrypted) file or message.

"Computing device" means a device having at least one processor and at least one memory device, wherein the processor can process data that can be stored in the memory device before and/or after processing, or a group of devices having that capacity in combination. By this definition, examples of a computing device include computer personal computer, palm computing device, notebook computer, server, mainframe, network of computing devices with coordinated processing or storage, network of components functioning together as a computing device wherein any single component may not be a computing device in its own right, etc. As another example, components of a computing device may be connected across the Internet. Other examples of computing devices could include boards, chips, exponentiators, multipliers, etc.

"Connection" means any connection that is adapted to carry communication, whatever the supporting technology. Examples of connections include hard wire connections such as phone lines, T1 lines, DSL, fiber optic, Ethernet, twisted pair, etc. Other examples of connections include wireless connections such as those operating by electromagnetic waves, wireless optics (e.g., infrared), etc. Further examples are a logical connection between two processes on the same system, and a connection between two processes sharing a common memory space.

"Cryptanalysis" means the art of breaking cryptosystems. It also means the process of looking for errors or weaknesses in the implementation of an algorithm or of the algorithm itself.

"Cryptography" is the art of creating and using cryptosystems.

"Cryptosystem" means the entire process of using cryptography. This includes the actions of encrypting and decrypting a file or message. It also means authenticating the sender of an e-mail message.

"Decryption" means any process to convert ciphertext back into plaintext. Decrypting is synonymous to decoding.

"DES" means the Data Encryption Standard. It is a cipher developed by the United States government in the 1970s to be the official encryption algorithm of the United States.

"Digital signature" means systems that allow people and organizations to electronically certify such features as their identity, their ability to pay, or the authenticity of an electronic document.

"Encryption" means any process to convert plaintext into ciphertext. Encrypting is synonymous to encoding.

"FTP" means File Transfer Protocol. FTP enables transferring of text and binary files over TCP connections. FTP allows transferring files according to a strict mechanism of ownership and access restrictions. It is now one of the most commonly used protocols over the Internet.

"Hamming weight" means the number of "1" bits in the binary representation of a number.

"HTTP" means Hyper Text Transfer Protocol. It is a protocol used to transfer hypertext pages across the World Wide Web.

"IP" means Internet Protocol, and is the underlying protocol for the other Internet protocols. IP defines the means to identify and reach a target computer on the network. A unique number known as an IP address identifies each computing device in the IP world.

"IPSec" means Internet Protocol Security. It is a standard for security at the network or packet-processing layer of network communication. IPSec provides two choices of security service: Authentication Header (AH), which essentially allows authentication of the sender of data, and Encapsulating Security Payload (ESP), which supports both authentication of the sender and encryption of data. IPSec is a suite of protocols that protect client protocols of IP, such as TCP. IPSec describes mechanisms that provide data source authentication, data integrity, confidentiality and protection against replay attacks. IPSec provides transport mode and tunnel mode operation. Some embodiments provide only tunnel mode operation, and others offers a more complete IPSec implementation.

"iSCSI" is a software package that emulates SCSI protocols, but the connection method is via an IP network instead of a direct SCSI compatible cable. This is one example of IP-based storage.

"Key" means a collection of bits, usually stored in a file, which is used to encrypt or decrypt a message.

"Network protocol" means a standard designed to specify how computers interact and exchange messages. It usually specifies the format of the messages and how to handle errors. The following Internet protocols are examples of network protocols: ARP, FTP, HTTP, IP, NNTP PPP, SLIP, SMTP, SNMP, TCP, Telnet, and UDP.

"NNTP" means Network News Transfer Protocol. It is a protocol used to carry USENET postings between News clients and USENET servers.

"PGP" means Pretty Good Privacy. It is a public-private key cryptosystem that allows users to more easily integrate the use of encryption in their daily tasks, such as e-mail protection and authentication, and protecting files stored on a computer. PGP is available for free to individual home users.

"Plaintext" means the original message or file. After a file or message has been encrypted and then decrypted you should end up with the original file or message.

"PPP" means Point-To-Point protocol, and is a protocol for creating a TCP/IP connection over both synchronous and asynchronous systems. PPP provides connections for host-to-network or router-to-router. It also has a security mechanism. PPP is well known as a protocol for connections over regular telephone lines using modems on both ends. This protocol is widely used for connecting personal computers to the Internet.

"Private key" means the private key of a public-private key cryptosystem. This key is used to digitally sign outgoing messages and is used to decrypt incoming messages.

"Public key" means the public key of a public-private key cryptosystem. This key is used to confirm digital signatures on incoming messages or to encrypt a file or message so that only the holder of the private key can decrypt the file or message.

"Public key cryptosystem" means an asymmetric encryption algorithm in which it is infeasible to derive one key from the other.

"Public-private key cryptosystem" means a cryptosystem that uses two different keys to encrypt and decrypt messages and files. The two keys are mathematically related to each other, but deriving one key from the other is infeasible. One key is a public key and one key is a private key. The public key is usually distributed to other users, and the private key is usually kept secret.

"Ring arithmetic" means an arithmetic of mathematical structures in which addition, subtraction, multiplication, and their obvious consequences such as exponentiation, have the properties and interrelationships usually encountered in high school algebra.

"SCSI" is an intelligent protocol that enables data blocks to be read at high speed from or sent at high speed to storage devices such as disks or tape drives. Early implementations of SCSI used ribbon cable and industry standard logic levels.

"Security association" means a relationship between two or more entities that describes how the entities will utilize security services to communicate securely. This relationship is represented by a set of information that can be considered a contract between the entities. The information must be agreed upon and shared between all the entities. Security association is commonly abbreviated SA.

"Shotgun multiplication" means a process like that described in this application for performing fast computations by performing processing in mathematically independent units, taking advantage of more than one basis and precomputed operands, and accommodating iterative problems.

"SLIP" means Serial Line Internet Protocol, and is a point-to-point protocol to use over a serial connection, a predecessor of PPP. There is also an advanced version of this protocol known as CSLIP (compressed serial line internet protocol) that reduces overhead on a SLIP connection by sending just header information when possible, thus increasing packet throughput.

"SMTP" means Simple Mail Transfer Protocol, and is dedicated to sending e-mail messages originating on a local host to a remote server over a TCP connection. SMTP defines a set of rules that allows two programs to send and receive e-mail over the network. The protocol defines the data structure to deliver with information regarding the sender, the recipient(s) and the e-mail's body.

"SNMP" means Simple Network Management Protocol. It is a simple protocol that defines messages related to network management. Through the use of SNMP, network devices such as routers can be configured by any host on their network.

"SSL" means Secure Sockets Layer, and is a trademark of Netscape. It is a program layer created by Netscape for managing the security of message transmissions in a network. The concept is that the programming for keeping messages confidential is to be contained in a program layer between an application (such as a Web browser or HTTP) and the Internet's TCP/IP layers. The "sockets" part of the term refers to the sockets method of passing data back and forth between a client and a server program in a network or between program layers in the same computer.

"SSL/TLS" means compatible with SSL and with TLS.

"Symmetric key" means the key of a symmetric key cryptosystem. The symmetric key is used to encrypt a file or message and also to decrypt the file or message.

"Symmetric key cryptosystem" means a cryptosystem that uses one key to lock and unlock—encrypt and decrypt—messages and files. The sender must posses the key to encrypt a file or message, and the recipient(s) must possess the key to decrypt the file or message.

"TCP" means Transmission Control Protocol. Like UDP, TCP is a protocol that enables a computer to send data to a remote computer. But unlike UDP, TCP is reliable—packets are guaranteed to wind up at their target in the correct order.

"Telnet" is a terminal emulation protocol for use over TCP connections. It enables users to login to remote hosts and use their resources from the local host.

"TLS" means Transport Layer Security. It is the successor protocol to SSL, created by the Internet Engineering Task Force (IETF) for general communication authentication and encryption over TCP/IP networks. TLS version 1 is nearly identical with SSL version 3, providing data integrity and privacy on a communications link over the Internet. It allows client-server applications to communicate and is designed to prevent eavesdropping, message forgery, and interference.

"TOE" means TCP Offload Engine. TOE technology typically takes the server CPU out of I/O processing by shifting TCP/IP processing tasks to a network adapter or storage device. This leaves the CPU free to run its applications, so users get data faster.

"Triple DES" means a method of improving the strength of the DES algorithm by using it three times in sequence with different keys.

"UDP" means User Datagram Protocol. It is a simple protocol that transfers datagrams (packets of data) to a remote computer. UDP doesn't guarantee that packets will be received in the order sent or that they will arrive at all.

What is claimed is:

1. An information-processing method including:
receiving a message;
ascertaining whether the message is in a selected application format;
if the message is not in the selected application format:
routing the message to a next location; and
if the message is in the selected format:
routing the message to a selected application processor;
processing the message by the selected application processor; and
routing the message to the next location;
wherein the selected application format relates to the encryption status of the message, and wherein the message has a property selected from the group consisting of: (a) the message is in the selected application format if it is not encrypted, and the message is not in the selected application format if it is encrypted, and (b) the message is in the selected application format if it is encrypted, and the message is not in the selected application format if it is not encrypted;
wherein receiving a packet or the message from a network includes receiving the packet from a packet switched network;
and processing the message by the selected application processor includes decrypting the message by the selected application processor;
wherein first and second iterations of the method are performed, and wherein the receiving a message of the second iteration corresponds to the routing of the message to a next location of the first iteration, whereby the message is processed in a pipeline fashion.

2. The method of claim 1, wherein receiving the message includes receiving the packet.

3. The method of claim 2, wherein receiving the packet includes receiving the packet from the network.

4. The method of claim 3, wherein the network is the Internet.

5. The method of claim 1, wherein
ascertaining whether the message is in the selected application format includes ascertaining whether the message is encrypted; and
processing the message by the selected application processor includes decrypting the message by the selected application processor.

6. The method of claim 1, wherein the message is in the selected application format if it is encrypted, and wherein the message is not in the selected application format if it is not encrypted.

7. The method of claim 1, wherein the message is in the selected application format if it is not encrypted, and wherein the message is not in the selected application format if it is encrypted.

8. An information-processing method, including:
receiving a message;
after receiving the message: ascertaining whether the message is susceptible to be processed by a particular application;
if the message is susceptible to be processed by the particular application:
routing the message to an application service device that is adapted to use the particular application to process the message;
after routing the message to the application service device:
processing the message by the application service device using the particular application;

after processing the message: routing the message to a next location; and if the message is not an application-specific message: routing the message to the next location;

wherein the particular application comprises a decryption application, wherein a message susceptible to by processed by the particular application comprises an encrypted message, wherein first and second iterations of the method are performed, and wherein the receiving a message of the second iteration corresponds to the routing of the message to the next location of the first iteration, whereby the message is processed in a pipeline fashion.

9. The information-processing method of claim 8, wherein the message is a packet.

10. A method for processing information, comprising:
receiving a packet in a packet filter from a switched network;
ascertaining whether the packet is in sequence or out of sequence;
if the packet is out of sequence:
routing the packet to a packet sequencer, and
routing the packet from the packet sequencer to a selected application processor; and
if the packet is in sequence:
routing the packet to a selected application processor;
processing the packet by the selected application processor; and
routing the packet to the next location;
wherein processing the packet by the selected application processor includes decrypting the packet, wherein first and second iterations of the method are performed, and wherein the receiving a message of the second iteration corresponds to the routing of the message to the next location of the first iteration, whereby the message is processed in a pipeline fashion.

* * * * *